United States Patent
Bryson et al.

(10) Patent No.: US 7,270,832 B2
(45) Date of Patent: Sep. 18, 2007

(54) COLLOIDAL SUSPENSION OF SUBMICRONIC PARTICLES FOR CARRYING ACTIVE PRINCIPLES AND THEIR MODE OF PREPARATION

(75) Inventors: Nathan Bryson, Millery (FR); Gérard Soula, Meyzieu (FR)

(73) Assignee: Flamel Technologies, Inc., Cedex (FR)

( * ) Notice: Subject to any disclaimer, the term of this patent is extended or adjusted under 35 U.S.C. 154(b) by 200 days.

(21) Appl. No.: 10/398,134

(22) PCT Filed: Oct. 5, 2001

(86) PCT No.: PCT/FR01/03083

§ 371 (c)(1),
(2), (4) Date: Apr. 1, 2003

(87) PCT Pub. No.: WO02/28521

PCT Pub. Date: Apr. 11, 2002

(65) Prior Publication Data

US 2004/0038885 A1 Feb. 26, 2004

(30) Foreign Application Priority Data

Oct. 6, 2000 (FR) .................................. 00/12837

(51) Int. Cl.
*A61K 9/10* (2006.01)
(52) U.S. Cl. .............................. 424/489; 514/2; 516/77
(58) Field of Classification Search ................ 424/489; 514/2
See application file for complete search history.

(56) References Cited

U.S. PATENT DOCUMENTS

| | | | |
|---|---|---|---|
| 4,351,337 A | 9/1982 | Sidman | |
| 4,450,150 A | 5/1984 | Sidman | |
| 5,286,495 A | 2/1994 | Batich et al. | |
| 5,449,513 A | 9/1995 | Yokoyama et al. | 424/78.08 |
| 5,510,103 A | 4/1996 | Yokoyama et al. | 424/78.08 |
| 5,780,579 A | 7/1998 | Soula et al. | |
| 5,904,936 A | 5/1999 | Huille et al. | |
| 6,180,141 B1 | 1/2001 | Lemercier et al. | 424/489 |
| 6,630,171 B1 | 10/2003 | Huille et al. | |
| 2001/0000510 A1 | 4/2001 | Sakurai et al. | 514/12 |

FOREIGN PATENT DOCUMENTS

| | | |
|---|---|---|
| EP | 0 583 955 A2 | 2/1994 |
| EP | 0 721 776 A1 | 7/1996 |
| WO | WO88/01213 | 2/1988 |
| WO | WO89/08449 | 9/1989 |
| WO | WO91/06286 | 5/1991 |
| WO | WO91/06287 | 5/1991 |
| WO | WO96/29991 | 10/1996 |
| WO | WO97/02810 | 1/1997 |
| WO | WO 01/37809 | 5/2001 |

OTHER PUBLICATIONS

Constancies A., (Journal of Colloid & Interface Science 217, 357-368, 1999).*
Chou, Peter Y. (Biochemistry 11(16), 3028-43, 1972).*
Akiyoshi, Chemistry Letters, vol. N8, 707-708, 1995.*
Candau, S., Chapter 3 of Light Scattering in Surfactant solutions, vol. 22, Ed. R. Zana, M. Dekker, Inc., New York (1984) pp. 147-207).*
Hayashi, Toshio (Polymer Journal (Tokyo, Japan) 17(12), 1273-80, 1985).*
Wojcik, J. (Macromolecules 23(15), 3655-62, 1990).*
Harada et al., "Formation of Polyion Complex Micelles in an Aqueous Milieu From a Pair of Oppositely-Charged Block Copolymers With Poly(ethylene Glycol)Segments," 28 *Macromolecules* 28 5294 (1995).
W.D. Fuller, *A procedure for the facile synthesis of amino-acid N-carboxyanhydrides*, Biopolymers (1976) vol. 15, pp. 1869-1871.
Harada et al., *Formation of Polyion Complex Micelles in an Aqueous Milieu from a Pair of Oppositely-Charged Block Copolymers with Poly(Ethylene Glycol) Segments*, Macromolecules, (1995) vol. 28, pp. 5294-5299.
M.J. Humphrey, *Delivery System for Peptide Drugs*, eds. S. Davis et al., Plenum Press, N.Y. (1986), pp. 139-151.
F. Touraud et al., copending U.S. Appl. No. 10/130,783, filed Aug. 5, 2002 as the National Stage of International Application No. PCT/FR00/02831.
Tsutsumiuchi et al., *Synthesis of Polyoxazoline—(Glyco)peptide Block Copolymer Ring-Opening Polymerization of (Sugar-Substituted) α Amino Acid N-Carboxyanhydrides with Polyoxazoline Macroinitiators*, Macromolecules (1997) vol. 30, pp. 4013-4017.
Akiyoshi et al. "Stabilization of insulin upon supramolecular complexation with hydrophobized polysaccharide nanoparticle" Chemistry letters N8: 707-708 (1995).
S. Candau, "Chapter 3, Light Scattering, In Surfactant Solutions" vol. 22 Ed. R. Zaria, M. Dekker, Inc. New York pp. 147-202 (1994).

* cited by examiner

*Primary Examiner*—David Lukton
(74) *Attorney, Agent, or Firm*—Patton Boggs, LLP (57) ABSTRACT

A suspension of biocompatible particles based on a double-block hydrophilic neutral polyaminoacid/hydrophobic neutral polyaminoacid copolymer and suitable for carrying active principles. The carrier particles can combine in colloidal suspension in a non-dissolved state with an active principle and release same, particularly in vivo, in prolonged and/or delayed delivery. The carrier particles may be derived from a powdery solid, and spontaneously form stable aqueous suspensions in the absence of surfactants or organic solvents. The invention also concerns the carrier particles in dry form, the method of preparing them, and pharmaceutical compositions (in dry form or suspension) which include the carrier particles associated with an active principle.

24 Claims, 1 Drawing Sheet

COLLOIDAL SUSPENSION OF SUBMICRONIC PARTICLES FOR CARRYING ACTIVE PRINCIPLES AND THEIR MODE OF PREPARATION

This application is a 371 of PCT/FR01/03083, filed Oct. 5, 2001, which claims priority to FR 00/12837, filed Oct. 6, 2000.

TECHNICAL FIELD

The present invention relates to the field of carrier particles (CP) that are useful for the administration of active principles (AP). The latter are preferably drugs or nutriments for administration to an animal or human organism by the oral or nasal, vaginal, ocular, subcutaneous, intravenous, intramuscular, intradermal, intra-peritoneal, intracerebral, parenteral or other route. However, they can also be cosmetic products or plant health products such as herbicides, pesticides, insecticides, fungicides, etc. In terms of their chemical nature, the AP to which the invention relates more particularly, but without implying a limitation, are e.g. proteins, glycoproteins, peptides, polysaccharides, lipopolysaccharides, oligo-nucleotides, polynucleotides and organic molecules.

The present invention relates more precisely to colloidal suspensions of carrier particles, advantageously of the submicron type, that are based on polyamino acids (PAA).

The present invention relates both to bare particles as such, and to AP carrier systems consisting of the particles loaded with the AP in question.

The present invention further relates to pulverulent solids comprising these CP.

The invention further relates to methods of preparing said colloidal suspensions of particles, with or without AP.

PRIOR ART

The purpose of encapsulating or adsorbing AP in CP is especially to modify their duration of action and/or convey them to the treatment site and/or increase the bioavailability of said AP. Numerous encapsulation techniques have already been proposed. The aim of such techniques is on the one hand to enable the AP to be transported to its site of therapeutic action while at the same time protecting it from the aggressions of the organism (hydrolysis, enzymatic digestion, etc.), and on the other hand to control the release of the AP at its site of action so that the amount available to the organism is maintained at the desired level. The AP involved in these changes in transport and residence in the organism are e.g. proteins, but they can also be products that are quite different from organic molecules of synthetic or natural origin. The review by M. J. HUMPHREY (Delivery system for peptide drugs, edited by S. DAVIS and L. ILLUM, Plenum Press, N.Y. 1986) discusses the problem associated with the improvement of AP bioavailability and the advantage of carrier and controlled release systems.

The CP according to the invention are of the type on which the AP is adsorbed.

Of all the materials that can be considered for forming CP, polymers are increasingly widely used because of their intrinsic properties. The specifications sheet which it is desired to obtain for the CP is particularly demanding and comprises the following specifications in particular:

1 The first specification sought for the CP would be that the polymer constituting the CP is biocompatible, capable of elimination (by excretion) and/or biodegradable, and particularly that it is metabolized to products that are non-toxic to the organism. In addition, the biodegradation in the organism should be of a sufficiently short duration.

2 It would be advantageous for the CP to be able to form a stable aqueous suspension without the aid of an organic solvent and/or a surfactant.

3 It would also be desirable for the CP to be sufficiently small to be able to undergo, in suspension in a liquid, a sterilizing filtration with a filter whose pore diameter is less than or equal to 0.2 µm.

4 It is desirable for the CP and the CP-AP systems to be obtainable by a method that is non-denaturing towards the AP.

5 The CP should advantageously make it possible to control the rate of release of the AP.

6 Another important specification would be for the CP-AP systems to be able to constitute excellent injectable drugs. This improved suitability for administration by injection—e.g. intravenous or intramuscular injection—or "injectability" is characterized by:
  (i) a reduced injected volume (for a given therapeutic dose), and
  (ii) a low viscosity.
  These two properties are satisfied when the therapeutic dose of AP is associated with a minimum amount of CP. In other words the CP must have a high AP loading factor.

7 The inherent cost of the CP in an injectable preparation must be reduced and, here again, the CP should have a high AP loading factor. In fact, the small size and high loading factor are major specifications sought for the CP.

8 It is also advantageous if the constituent polymer of the CP does not induce an immune response.

The earlier technical proposals, described below, attempted to meet all these specifications. The earlier proposals (a) to (h) will be mentioned by way of illustration:

(a) Patent U.S. Pat. No. 5,286,495 relates to a method of encapsulation by the vaporization of proteins in the aqueous phase with the aid of materials carrying opposite charges, namely alginate (negatively charged) and polylysine (positively charged). This manufacturing process makes it possible to produce particles with a size above 35 µm.

b) Furthermore, emulsion techniques are commonly used to prepare microparticles loaded with AP. For example, patent applications WO 91/06286, WO 91/06287 and WO 89/08449 disclose such emulsion techniques in which organic solvents are used to solubilize polymers, for example of the polylactic type. However, it has been found that the solvents can be denaturing, especially for peptide or polypeptide AP.

(c) Biocompatible CP called proteinoids are also known, having been described since 1970 by X. FOX and K. DOSE in "Molecular evolution and the origin of life", published by Marcel DEKKER Inc. (1977). Thus patent application WO 88/01213 proposes a system based on a mixture of synthetic polypeptides whose solubility depends on the pH. To obtain the matrix microparticles according to said invention, the authors solubilize the mixture of polypeptides and then, with a pH change, they cause proteinoid particles to precipitate. When the precipitation takes place in the presence of an AP, the latter is encapsulated in the particle.

(d) Patent U.S. Pat. No. 4,351,337, which relates to a different field from that of AP transport peculiar to the present invention, may also be cited as a matter of interest. Said patent discloses mass implants fixed and localized in very specific places in the organism. These implants are tubes or hollow capsules of microscopic size (160 μm, with a length of 2000 μm) which consist of polyamino acid copolymers—e.g. poly(glutamic acid/leucine) or poly(benzyl glutamate/leucine) copolymers—obtained by the copolymerization of amino acid N-carboxy anhydride (NCA) monomers. An AP is included by a technique of solvent evaporation from a mixture of polymer and AP. Patent U.S. Pat. No. 4,450,150 belongs to the same family as patent U.S. Pat. No. 4,351,337 studied above, and has essentially the same subject matter. The constituent PAA are poly(glutamic acid/ethyl glutamate) copolymers.

(e) Patent application EP 0 734 720 relates to polyamino acid particles that are useful for carrying AP. These particles have a size of between 10 and 500 nm, preferably of between 30 and 400 nm.

The particles according to EP 0 734 720 are formed spontaneously when PAA are brought into contact with an aqueous solution. The PAA include hydrophobic neutral amino acid monomers, AANO (Leu, Ile, Val, Ala, Pro, Phe), and hydrophilic ionizable monomers, AAI (Glu, Asp). These PAA are prepared by copolymerizing NCA of AAI precursors (e.g. Glu-OMe) and NCA of AAO (e.g. Leu) in solution in a dioxane/toluene mixture. The poly(Glu-OMe/Leu) copolymer obtained in solution is recovered by precipitation in water, filtration and drying. This copolymer is then subjected to acid hydrolysis by being incorporated into trifluoroacetic acid (TFA), in which it dissolves. A poly(Glu-O—Na/Leu) copolymer is recovered after neutralization, dialysis, filtration and lyophilization.

The coPAA is dispersed in an aqueous solution of NaCl and a suspension of nanoparticles forms spontaneously. As soon as these CP in aqueous suspension are brought into contact with an AP, the latter associates spontaneously with the CP by adsorption. The CP have a hydrophobic core formed of hydrophobic amino acids and a hydrophilic external "lattice" based on hydrophilic amino acids.

It is pointed out that the carrier particles according to EP 0 734 720 contain ionizable amino acids (Glu) carrying a negative stabilizing electric charge, making it possible to prevent the particles, CP, from flocculating and aggregating.

(f) FR-A-2 746 035 relates to microparticles of composite gel that are physicochemically stable, integral and capable of being used as active principle carriers. These microparticles consist of oil (I), aqueous phase (II) and at least one linear, non-crosslinked, synthetic copolyamino acid (III) containing at least two different types of amino acid comonomers: hydrophilic, AAI, and hydrophobic, AAO. The AAI can be Glu, Asp, Orn, Arg, Lys, Asn, His and associations thereof. The AAO comonomers can be Leu, Tyr, Phe, Val, Cys, Ile and associations thereof. On page 27, lines 8 to 18, in particular, FR-A-2 746 035 describes an aqueous colloidal suspension of polyamino acids, for example poly(leucine/sodium glutamate) copolymer.

However, FR-A-2 746 035 does not disclose the use of the copolymers by themselves as a nanoparticulate pharmaceutical system for carrying AP. The AAI of FR-A-2 746 035 are not hydrophilic neutral amino acids selected from the group comprising:

the following natural neutral amino acids: serine, threonine, hydroxyproline, glutamine;

the following rare or synthetic neutral amino acids: methionine S-oxide, O-glycosidylserine; and the following derivatives of neutral amino acids: N-hydroxyethyl-glutamine, N-hydroxypropylasparagine.

All these earlier technical proposals described above:

either incompletely meet the specifications of the specifications sheet indicated above, particularly as regards suitability for sterilization by filtration, high degradation rate, adaptability to the constraints of drug administration by injection, low cost and high AP loading factor;

or could be replaced by novel technical solutions capable of affording novel advantages (prior art reference EP 0 734 720).

BRIEF DISCLOSURE OF THE INVENTION

With these facts established, one essential objective is to be able to provide novel CP which form stable aqueous suspensions of CP spontaneously, without the aid of surfactants or organic solvents.

Another essential objective of the present invention is to provide novel CP in stable colloidal aqueous suspension or in pulverulent form, based on polyamino acids (PAA), these novel CP preferably meeting specifications 1 to 8 of the specifications sheet mentioned above.

Another essential objective of the invention is to improve the particles disclosed in PCT patent application WO 96/29991.

Another essential objective of the invention is to provide a novel suspension of CP whose characteristics are perfectly controlled, especially in terms of the AP loading factor and in terms of control of the AP release kinetics.

Another essential objective of the invention is to provide injectable medicinal suspensions. The specifications required for such suspensions are a small injection volume and a low viscosity. It is important that the mass of colloidal particles per injection dose be as small as possible, without limiting the amount of active principle, AP, transported by these particles, so as not to detract from the therapeutic efficacy.

Another essential objective of the invention is to provide a colloidal aqueous suspension or a pulverulent solid which comprises active principle carrier particles meeting the above-mentioned specifications, and which constitutes an appropriate galenical form suitable for administration, for example orally, to humans or animals.

Another essential objective of the invention is to provide a colloidal suspension comprising active principle carrier particles that can be filtered on 0.2 μm filters for sterilization purposes.

Another essential objective of the invention is to propose a method of preparing PAA particles (dry or in suspension in a liquid) that are useful especially as active principle carriers, said method being simpler to carry out and non-denaturing towards the active principles and additionally always allowing fine control over the mean size of the particles obtained.

Another essential objective of the invention is to use the above-mentioned particles, in aqueous suspension or in solid form, for the preparation of drugs (e.g. vaccines), especially for oral, nasal, vaginal, ocular, subcutaneous, intravenous, intramuscular, intradermal, intraperitoneal, intracerebral or parenteral administration, it being possible in particular for the active principles of these drugs to be proteins, glycoproteins, peptides, polysaccharides, lipopolysaccharides, oligonucleotides and polynucleotides;

and/or nutriments;

and/or cosmetic or plant health products;

and/or medicinal organic molecules.

Another essential objective of the present invention is to provide suspensions of submicron CP based on PAA that are capable of acting as a carrier for an AP, particularly a medicinal AP for administration to a human or animal organism, or alternatively a nutritional, plant health or cosmetic AP.

Another objective of the present invention is to provide a drug, of the type consisting of a system for the prolonged release of active principles, which is easy and economic to produce and which is also biocompatible and capable of assuring a very high level of bioavailability of the AP.

Another essential objective of the invention is to provide a vaccine carrier system which is non-immunogenic intrinsically and in combination with one or more antigens.

The product-related objectives (among others) are achieved by the present invention, which relates first and foremost to a stable colloidal suspension of submicron structured particles capable of being used especially for carrying one or more active principles, AP, these particles being individualized (discrete) supramolecular arrangements that are:

based on linear amphiphilic polyamino acids (PAA) having peptide linkages and comprising at least two different types of hydrophilic repeating amino acids, AAI, and hydrophobic repeating amino acids, AAO, the amino acids of each type being identical to or different from one another;

capable of associating at least one AP in colloidal suspension, in the undissolved state, and releasing it, especially in vivo, in a prolonged and/or delayed manner;

and stable in the aqueous phase at a pH of between 4 and 13, in the absence of surfactant(s), characterized:

in that the hydrophilic repeating amino acids, AAI, are hydrophilic neutral amino acids, AANI, with the exclusion of asparagine;

in that the hydrophobic repeating amino acids, AAO, are hydrophobic neutral amino acids, AANO;

and in that the repeating amino acids of each type, AANI and AANO, are identical to or different from one another.

DETAILED DISCLOSURE OF THE INVENTION

One of the main inventive aspects of these novel carrier particles, CP, in stable colloidal aqueous suspension or in the form of a pulverulent solid, concerns the novel selection of a group of polymers and a novel methodology for obtaining particles of submicron size which form a stable colloidal aqueous suspension in the absence of surfactants or solvents.

Another main inventive aspect of these novel carrier particles, CP, in stable colloidal aqueous suspension or in the form of a pulverulent solid, concerns the novel selection of two neutral amino acids as hydrophilic repeating monomers, AANI, and hydrophobic repeating monomers, AANO.

Now, contrary to what those skilled in the art might have feared, not having ionizable hydrophilic amino acids, AAII, i.e. negative charges, as in the particles according to WO 96/29991, does not detract from the stability. In fact, contrary to all expectations, the colloidal suspension according to the present invention does not flocculate. The particles based on poly(AANI/AANO) do not self-aggregate. Moreover, it was not at all obvious a priori that these particles of poly(AANI/AANO) would be capable of associating spontaneously with active principles, AP, and releasing these AP at the sites of therapeutic action.

The structure of the PAA polymers and the nature of the neutral amino acids are chosen so that:

the polymer chains spontaneously organize themselves into small particles (CP);

the particles form a stable colloidal suspension in water and in a physiological medium;

the CP associate with proteins or other AP in aqueous media by a spontaneous mechanism that is non-denaturing towards the protein; and the CP release the AP in a physiological medium and, more precisely, in vivo; the release kinetics depend on the nature of the PAA polymer that is the CP precursor.

Thus, by varying the specific structure of the PAA, it is possible to control the AP association and release phenomena from the kinetic and quantitative points of view.

It is to the Applicant's credit to have chosen, as the constituent material of the CP, a specific composition of neutral polyamino acids which are amphiphilic and therefore possess properties of CP made of PAA, namely:

the possibility of spontaneously forming colloidal suspensions of CP that are compatible with the pH of the physiological media encountered in the intended therapeutic applications;

spontaneous association of the AP with CP in the absence of any agent other than water, which acts as solvent and, in the case of proteins, is non-denaturing;

the possibility of releasing the AP from the AP-CP association complex under physiological conditions with pharmacokinetic and pharmacodynamic profiles which lead to the expectation of valuable uses in the therapeutic field (AP transport);

filterability with a cut-off threshold less than or equal to 0.2 μm for sterilization purposes;

improved biodegradability; and optimized injectability.

These PAA can be of the ordered type with alternate sequences (blocks) or of the disordered type with random sequences.

Thus, in a first embodiment of the CP according to the invention, the constituent PAA are of the "block" type and are characterized by a molar ratio AANO/(AANI+AANO) which is such that:

AANO/(AANI+AANO)$\geq$6%,

10% $\leq$AANO/(AANO+AANI)$\geq$70%, preferably, 20% $\leq$AANO/(AANI+AANO)$\leq$60%, and particularly preferably, 35% $\leq$AANO/(AANI+AANO)$\leq$50%.

Advantageously, the absolute length of each block of AANO, expressed as the number of AANO, is such that:

AANO$\geq$5, preferably, AANO $\geq$10, and particularly preferably, AANO $\geq$20.

In a second embodiment of the CP according to the invention, the constituent PAA are of the "random" type, i.e.

prepared by the simultaneous copolymerization of AANI and AANO monomers, and the molar ratio AANO/(AANO+AANI) is such that:

AANO/(AANO+AANI)≧10%,
preferably, AANO/(AANO+AANI)≧20%,
and particularly preferably, 30% ≦AANO/(AANI+AANO)≦70%.

Advantageously, the molecular weight, Mw, of these random PAA is such that:

Mw≧2000 g/mol,
preferably, Mw≧5500 g/mol,
and particularly preferably, 5500 g/mol ≦Mw≦200,000 g/mol.

According to a preferred characteristic of the invention, the block or random PAA constituting the particles have degrees of polymerization, DP, of between 30 and 600, preferably of between 50 and 200 and particularly preferably of between 60 and 150.

Advantageously, the PAA constituting the particles, CP, are "di-block" PAA.

Preferably, the hydrophilic AANI is (are) selected from the group comprising:

natural neutral amino acids, preferably those selected from the group comprising serine, threonine, hydroxyproline and glutamine;
the rare or synthetic neutral amino acids, preferably those selected from the group comprising methionine S-oxide and O-glycosidylserine; and
derivatives of neutral amino acids, preferably those selected from the group comprising N-hydroxyethylglutamine, N-hydroxypropylasparagine, N-hydroxyethylasparagine and N-hydroxypropylglutamine.

Advantageously, the hydrophobic AANO is (are) selected from the group comprising:

natural neutral amino acids, preferably those selected from the group comprising Leu, Ile, Val, Ala, Pro and Phe;
rare or synthetic neutral amino acids, preferably those selected from the group comprising norleucine and norvaline; and
derivatives of polar amino acids, preferably those selected from the group comprising methyl glutamate, ethyl glutamate, benzyl aspartate and N-acetyllysine.

According to an advantageous characteristic, the carrier particles (CP) of the suspension have a mean size of between 0.01 and 0.5 µm, preferably of between 0.01 and 0.2 µm.

Another preferred characteristic of the suspension is that it is aqueous and stable.

The present invention relates not only to suspensions of bare particles as defined above, but also to suspensions of particles comprising at least one active principle, AP. Preferably, the suspension according to the invention is aqueous and stable. These particles, whether loaded with AP or not, are advantageously in a form dispersed in a liquid (suspension), preferably an aqueous liquid, but can also be in the form of a pulverulent solid obtained from the suspension of CP as defined above.

It follows from this that the invention relates not only to a colloidal (preferably aqueous) suspension of CP, but also to a pulverulent solid comprising CP which is obtained from the suspension according to the invention.

Another essential object of the invention concerns the preparation of:

selected particles as described above;
and other selected particles which are structured, submicron and capable of being used especially for carrying one or more active principles, AP, these particles being individualized (discrete) supramolecular arrangements that are:

based on linear amphiphilic polyamino acids (PAA) having peptide linkages and comprising at least two different types of hydrophilic repeating amino acids, AAI, and hydrophobic repeating amino acids, AAO, the amino acids of each type being identical to or different from one another;
capable of associating at least one AP in colloidal suspension, in the undissolved state, and releasing it, especially in vivo, in a prolonged and/or delayed manner;
and stable in the aqueous phase at a pH of between 4 and 13, in the absence of surfactant(s), where:

the hydrophilic repeating amino acids, AAI, consist at least partly of asparagine;
and the hydrophobic repeating amino acids, AAO, are hydrophobic neutral amino acids, AANO, which are identical to or different from one another, it being possible for these particles to be either in the form of a colloidal suspension or in the form of a pulverulent solid obtained from a stable colloidal suspension of particles.

The method of preparation in question consists essentially in synthesizing precursor PAA and converting them to structured particles.

More precisely, the method of preparation is first and foremost a method of preparing submicron structured particles capable of being used especially for carrying one or more active principles, these particles being discrete supramolecular arrangements that are:

based on linear amphiphilic polyamino acids (PAA) having peptide linkages and comprising at least two different types of hydrophilic repeating amino acids, AAI, and hydrophobic repeating amino acids, AAO, the amino acids of each type being identical to or different from one another;

capable of associating at least one AP in colloidal suspension, in the undissolved state, and releasing it, especially in vivo, in a prolonged and/or delayed manner;

and stable in the aqueous phase at a pH of between 4 and 13, in the absence of surfactant(s).

This method is characterized in that:

1) a copolymerization is carried out between monomers formed of amino acid N-carboxy anhydrides (NCA) of at least two different types:

on the one hand starting NCA monomers comprising NCA-Glu-OR and/or NCA-Asp-OR and/or NCA-AANI,
and on the other hand NCA-AANO, in the presence of:
at least one non-aromatic polar solvent preferably selected from the group comprising N-methylpyrrolidone (NMP), dimethylformamide (DMF), dimethyl sulfoxide (DMSO), dimethylacetamide (DMAc) and pyrrolidone, NMP being more particularly preferred;
and optionally at least one cosolvent selected from aprotic solvents (preferably 1,4-dioxane) and/or protic solvents (preferably pyrrolidone) and/or water and/or alcohols, methanol being particularly preferred;

2) in the case where the starting NCA monomers are NCA-Glu-OR and/or NCA-Asp-OR (R=alkyl), an aminolysis is carried out which consists in bringing the copolymer obtained in step 1 into contact with an aqueous phase comprising at least one amine, and which makes it possible to convert Glu-OR to Gln and Asp-OR to Asn;
3) the reaction medium is optionally dialyzed to purify the aqueous suspension of structured particles;
4) this suspension of step 3 is optionally concentrated; and
5) the liquid medium is removed so that the pulverulent solid comprising the particles can be collected.

The first step of the method is based on the known techniques of polymerizing α-amino acid N-carboxy anhydrides (NCA), which are described for example in the article "Biopolymers, 15, 1869 (1976)" and in the work by H. R. KRICHELDORF entitled "α-Amino acid N-carboxy anhydride and related heterocycles", Springer Verlag (1987).

Using carefully chosen polar, non-aromatic aprotic copolymerization solvents that avoid any precipitation, and using acid hydrolysis in the presence of water and a non-aromatic, polar organic solvent, affords submicron, discrete structured particles with a high AP loading capacity which form a stable colloidal suspension in aqueous media. These particles are in no way comparable to a macroscopic agglomerated precipitate of the kind referred to above in respect of earlier proposal (d).

In one variant, after step 1, the poly(AANO/AANI) copolymer obtained is precipitated—preferably in water—and this precipitate is collected. This variant corresponds to a batch mode of preparing particles in which the poly-(AANO/AANI) copolymer is isolated in the form of a precipitate constituting a stable intermediate. This precipitate can be filtered off, washed and dried, for example.

Particularly preferably, the NCA-pAAI are NCA of O-alkylated glutamic or aspartic acid, for example NCA-Glu-O-Me, NCA-Glu-O-Et or NCA-Glu-O-Bz (Me=methyl—Et=ethyl—Bz=benzyl).

In known manner, the copolymerization takes place at a temperature of between 20 and 120° C., at atmospheric pressure and in the presence of an amine initiator, e.g. $NH_3$.

Other experimental parameters, such as the concentration of NCA and/or polymer in the non-aromatic polar solvent (preferably NMP) and/or the concentration or nature of the protic cosolvent, during the synthesis, will be adjusted according to the desired effects known to those skilled in the art.

The acid hydrolysis (step 2) is carried out with water and at least one mineral acid such as phosphoric or hydrochloric acid—the latter being preferred—and/or at least one organic acid such as trifluoroacetic acid (TFA), acetic acid, dichloroacetic acid or organosulfonic acids.

The proportions of water/acid—expressed in parts by weight—in an acidic aqueous hydrolysis phase are advantageously:
from 60/1 to 2/1,
preferably 40/1 to 2/1,
and particularly preferably 20/1 to 2/1.

The proportions of acidic aqueous hydrolysis phase/NMP—expressed in parts by weight—are advantageously:
from 5/100 to 200/100,
preferably 10/100 to 100/100,
and particularly preferably from 20/100 to 80/100.

Other parameters, such as the polymer concentration, the temperature of the reaction mixture, the mode of addition of the acidic aqueous hydrolysis phase, the use of reduced pressure, the reaction time, etc., are adjusted according to the desired effects well known to those skilled in the art.

In practice, the neutralization (step 3) is carried out e.g. with sodium hydroxide.

The salt formed at the end of the neutralization, and the solvent, are then removed by any appropriate physical separation treatment, for example by diafiltration (dialysis) (step 4), filtration, pH modification, chromatography, etc.

This yields an aqueous suspension of structured particles which can be concentrated, for example by distillation or any other suitable physical means such as ultrafiltration or centrifugation.

In step 6, to separate the particles from their liquid suspension medium, the aqueous phase is optionally removed, for example by drying (e.g. in an oven), lyophilization or any other suitable physical means such as ultrafiltration or centrifugation. A white pulverulent solid is recovered at the end of this step 6.

In one variant, the concentration step can be carried out by means of a chemical treatment, such as a lowering of the pH, which converts the hydrophilic part of the glutamate monomers to acid, making them insoluble in water. These acidic PAA intermediates can be filtered off, washed and dried. Said acidic intermediates can be neutralized with a chemical base in a subsequent step to give a suspension of particles.

It is pointed out that the implementation of steps 1, 2, 3, 4 and optionally 5 of the above method corresponds to a preparation of a colloidal suspension of submicron particles with a high AP loading factor.

In this preparation of a colloidal suspension, the amphiphilic PAA, poly(AANO/AANI), of step 2 are placed in an aqueous medium in which at least part of the AANI is soluble and at least part of the AANO is insoluble. The PAA exist in the form of nanoparticles in this aqueous medium.

An alternative preparation of the suspension of CP according to the invention consists in bringing the pulverulent solid, as described above as a product and by its method of preparation, into contact with an aqueous medium that is a non-solvent for the AANO.

One or more AP can be associated with the particles by using several methods according to the invention. Non-limiting examples of these methods are listed below.

According to a first method, an AP is associated with the particles by bringing a liquid phase (aqueous or non-aqueous) containing the AP into contact with the colloidal suspension of particles which may or may not comprise Asp as AANI.

According to a second method, the AP is associated with the particles by bringing an AP in the solid state into contact with the colloidal suspension of particles which may or may not comprise Asp as AANI. The solid AP can be e.g. in the form of a lyophilizate, precipitate or powder or in another form.

According to a third method, the pulverulent solid (PAA which may or may not comprise Asp as AANI), as described above as a product and by its preparative characteristics, is brought into contact with a liquid phase (aqueous or non-aqueous) containing the AP.

According to a fourth method, the pulverulent solid, as described above as a product and by its preparative characteristics (PAA which may or may not comprise Asp as AANI), is brought into contact with the AP in solid form. This mixture of solids is then dispersed in a liquid phase, preferably an aqueous solution.

In all these methods, the AP used can be in the pure form or a preformulated form.

Given the nanometric size of the particles, the suspension can be filtered on sterilization filters, enabling sterile injectable medicinal liquids to be obtained easily and at lower cost. The ability, afforded by the invention, to control the particle size and reach Dh values of between 25 and 100 nm is an important asset.

The present invention further relates to novel intermediates of the method described above, characterized in that they consist of PAA copolymers (which may or may not comprise Asp as AANI) that are particle precursors.

INDUSTRIAL APPLICATION

According to another of its features, the invention relates to a suspension and/or a pulverulent solid (PAA which may or may not comprise Asp as AANI) as defined above and/or as obtained by the method described above, this suspension and this solid comprising at least one active principle preferably selected from:
vaccines;
proteins and/or peptides, among which the following are more preferably selected: hemoglobins, cytochromes, albumins, interferons, antigens, antibodies, erythropoietin, insulin, growth hormones, factors VIII and IX, interleukins or mixtures thereof, and hemopoiesis-stimulating factors;
polysaccharides, heparin being more particularly selected;
nucleic acids and preferably RNA and/or DNA oligonucleotides;
non-peptido-protein molecules belonging to various anti-cancer chemotherapy categories, particularly anthracyclines and taxoids;
and mixtures thereof.

The invention further relates to a suspension and/or a pulverulent solid (PAA which may or may not comprise Asp as AANI) loaded with a nutritional, plant health or cosmetic AP.

Finally, the invention relates to a pharmaceutical, nutritional, plant health or cosmetic proprietary product, characterized in that it contains a suspension and/or pulverulent solid as defined above, loaded with AP.

According to another of its objects, the invention further relates to the use of these CP (in suspension or in solid form: PAA which may or may not comprise Asp as AANI), loaded with AP, for the manufacture of drugs of the type consisting of systems for the controlled release of AP.

In particular, the invention relates to the use of a stable colloidal suspension of submicron structured particles loaded with one or more active principles, AP, these particles being individualized (discrete) supramolecular arrangements that are:
based on linear amphiphilic polyamino acids (PAA) having peptide linkages and comprising at least two different types of hydrophilic repeating amino acids, AAI, and hydrophobic repeating amino acids, AAO, the amino acids of each type being identical to or different from one another;
capable of associating at least one AIP in colloidal suspension, in the undissolved state, and releasing it, especially in vivo, in a prolonged and/or delayed manner;
and stable in the aqueous phase at a pH of between 4 and 13, in the absence of surfactant(s),
where:
the hydrophilic repeating amino acids, AAI, consist at least partly of asparagine;
and the hydrophobic repeating amino acids, AAO, are hydrophobic neutral amino acids, AANO, which are identical to or different from one another,
for the preparation of an aqueous suspension or a pulverulent solid as above defined, loaded with at least one AP.

Examples of drugs are those that can preferably be administered by the oral, nasal, vaginal, ocular, subcutaneous, intravenous, intramuscular, intradermal, intra-peritoneal, intracerebral or parenteral route.

Examples of cosmetic applications that can be considered are compositions which comprise an AP associated with the CP according to the invention and which can be administered transdermally.

Examples of possible plant health products are herbicides, pesticides, insecticides, fungicides, etc.

The Examples which follow will provide a better understanding of the invention according to its different product/method/application features. These Examples illustrate the preparation of particles of polyamino acids which may or may not be loaded with active principles, and also present the structural characteristics and the properties of these particles.

EXAMPLES

Example 1

Preparation of Poly(Leucine/Methyl Glutamate) Block Copolymer

The techniques used to polymerize NCA to polymers with block or random structures are known to those skilled in the art and are described in detail in the work by H. R. KRICHELDORF entitled "α-Amino acid N-carboxy anhydrides and related heterocycles", Springer Verlag (1987). The synthesis of one such polymer is specified below.

Synthesis of poly(Leu)$_{40}$-poly(GluOMe)$_{80}$: 10 g of NCA-GluOMe are solubilized in 150 ml of NMP at 60° C. 5 ml of a solution of 0.91 g of benzylamine in 50 ml of NMP are added all at once to the monomer. After 1 h, 14.1 g of NCA-Leu, previously solubilized in 20 ml of NMP, are added. Polymerization continues for a further 3-4 h.

Sampling of the reaction medium affords the following characterizations: Yield: 90%. Composition by $^1$H NMR (TFA-d): 66 mol % of GluOMe. Reduced viscosity (0.5% of TFA at 25° C.): 0.4 dl/g. Molecular weight by GPC: 20,000 g/mol.

Example 2

Aminolysis of Poly(Leucine/Methyl Glutamate) Block Copolymer with Hydroxyethylamine 10 g of hydroxyethylamine are added all at once to the NMP solution of polymer prepared according to Example 1. The medium is heated to 80° C. and kept at this temperature for 2 days. 150 ml of water are then added to the polymer solution, which is then purified by a dialysis step to ensure removal of the excess amine and the NMP. Finally, the particles are isolated by lyophilization.

Yield: quantitative. $^1$H NMR (TFA-d): 8% of residual methoxy (3.5 ppm); 92% of hydroxyethylglutamine. Composition by $^1$H NMR (TFA-d): 34% of Leu. Particle size (light scattering, QLS mode): 100 nm.

Example 3

Demonstration of Nanoparticles by Light Scattering (LS) and Transmission Electron Microscopy (TEM)

10 mg of particles of polymer 1 are suspended in 10 ml of water or an aqueous solution of salt. This solution is then introduced into a Coulter granulometer (or laser diffractometer). The results of particle size analysis of the different products tested are shown in Table 1 below.

TABLE 1

Measurement of the size of the CP

| Example | Polymer | Size (nm) |
|---------|---------|-----------|
| 2 | poly[(Leu)$_{0.66}$]-poly[(Gln-N-hydroxyethyl)$_{0.37}$]$_x$ block copolymer | 100 |

Example 4

Test of Association of Nanoparticles with a Protein (Insulin)

An isotonic phosphate buffer solution of pH 7.4 is used to prepare a solution of human insulin containing 1.4 mg/ml, corresponding to 40 IU/ml. 10 mg of the CP prepared in Example 1 are dispersed in 1 ml of this insulin solution. After 15 hours of incubation at room temperature, the insulin associated with the CP and the free insulin are separated by centrifugation (60,000 g, 1 hour) and ultrafiltration (filtration cut-off: 300,000 D). The free insulin recovered from the filtrate is assayed by HPLC or ELISA and the amount of associated insulin is deduced by difference. The amount of insulin associated with the CP is greater than 0.77 mg, representing more than 55% of the total insulin used.

The Table below collates the results of the measurements of degree of association performed on different CP. The degree of association expresses the percentage of associated insulin relative to the insulin used in a preparation containing 1.4 mg/ml of insulin and 10 mg/ml of CP. This value is converted to a loading factor which expresses a formulation with 100% protein binding, in mg of insulin per 100 mg of CP.

TABLE 2

Measurement of the degree of association with insulin for a mixture of 0.14 mg INSULIN/mg CP

| Example | Polymer | Degree of association (%) | Loading factor mg/100 mg CP |
|---------|---------|---------------------------|------------------------------|
| 2 | poly[(Leu)$_{0.66}$]-poly[(Gln-N-hydroxyethyl)$_{0.37}$]$_x$ block copolymer | 99 | 13.6 |

Example 5

Figure 1:
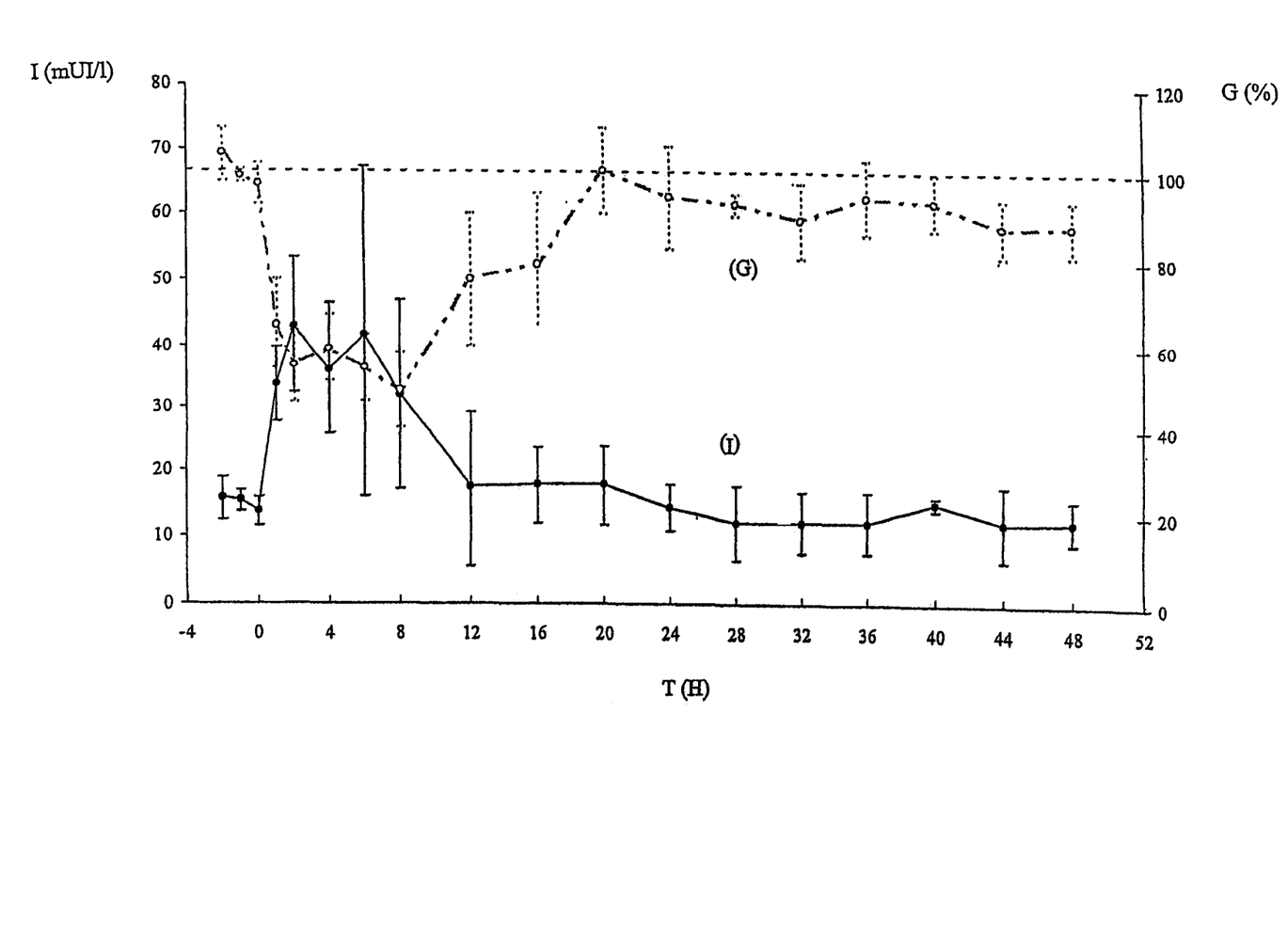
FIG. 1 shows the time course of release of insulin in vivo from the carrier particles of Example 1.

Pharmacokinetics and Pharmacodynamics of Insulin-loaded CP in Fasted Healthy Dogs The particle+insulin preparation of Example 4 was injected into dogs which had been rendered diabetic by total pancreatectomy and fasted since the previous evening. At 11 am the preparation was administered subcutaneously into the thorax at a dose of 0.5 IU of insulin per kg of live weight of the animal. The volume administered is between 0.18 and 0.24 ml. At the times −4, −2, 0, 1, 2, 4, 6, 8, 12, 16, 20, 24, 28, 32, 36, 40, 44 and 48 hours, 1 ml of blood is taken by jugular puncture under vacuum into a sodium heparinate tube. 30 µl of whole blood are used immediately to measure the glycemia. The tube is then centrifuged, the supernatant is decanted and the plasma is stored at −20° C. to assay the insulin. The results shown in FIG. 1 below show that the insulin is released up to 12 hours (solid line) and that there is a substantial hypoglycemic effect extending up to 20 hours (broken line) after injection.

TABLE 3

Measurement of the duration of action of insulin (hypoglycemic effect) in the presence of CP according to the invention

| Example | Polymer | Time to return to basal level (h) |
|---------|---------|-----------------------------------|
|  | soluble insulin (without CP) | 1 |
| 2 | poly[(Leu)$_{0.66}$]-poly[(Gln-N-hydroxyethyl)$_{0.37}$]$_x$ block copolymer | 20 |

This Example demonstrates the non-denaturation of insulin in the presence of CP according to the invention.

Also, Example 2 makes it possible to demonstrate the increase in the duration of action of insulin compared with non-formulated insulin, and hence the usefulness of the CP as a delaying system for the controlled release of insulin. It also shows how it is possible to control the duration of action by the appropriate choice of hydrophobic group.

Example 6

Aminolysis of Poly(Phenylalanine/Methyl Glutamate) Block Copolymer with Hydroxyethylamine 10 g of hydroxyethylamine are added all at once to the NMP solution of polymer prepared according to Example 1 using the monomers NCA-GluOMe and NCA-phenylalanine. The medium is heated to 80° C. and kept at this temperature for 2 days. 150 ml of water are then added to the polymer solution, which is then purified by a dialysis step to ensure removal of the excess amine and the NMP.

Finally, the particles are isolated by lyophilization.

Yield: quantitative. $^1$H NMR (TFA-d): 6% of residual methoxy (3.5 ppm); 94% of hydroxyethylglutamine. Composition by $^1$H NMR (TFA-d): 34% of Leu. Particle size (light scattering, QLS mode): 100 nm.

Example 7

Aminolysis of Poly(Leucine/Benzyl Glutamate) Block Copolymer with 3-aminopropylene-1,2-glycol 10 g of 3-aminopropylene-1,2-glycol are added all at once to the NMP solution of polymer prepared according to Example 1 using the monomers NCA-GluOBzl and NCA-Leu. The medium is heated at 80° C. for 2 days. 150 ml of water are then added to the polymer solution, which is then purified by a dialysis step to ensure removal of the excess amine and the solvent. Finally, the particles are isolated by lyophilization.

Yield: quantitative. Particle size (QLS, according to Example 3): 100 nm.

Example 8

Test of Association of Nanoparticles with a Protein (Insulin)

According to Example 4, the isolated particles of Example 6 and human insulin are used to give a loading factor expressed in mg of insulin per 100 mg of CP.

| Example | Polymer | Degree of association | Loading factor in mg/100 mg CP |
|---|---|---|---|
| 6 | poly[(Phe)$_{0.79}$]-poly[(Gln-N-dihydroxypropyl)$_{0.21}$]$_x$ block copolymer | 99 | 8.5 |
| 7 | poly[(Leu)$_{0.66}$]-poly[(Gln-N-dihydroxypropyl)$_{0.33}$]$_x$ block copolymer | 99 | 13.7 |

The invention claimed is:

1. A stable colloidal suspension comprising submicron particles, wherein the particles:
   are individualized supramolecular arrangements comprising linear, peptide-linked, amphiphilic polyamino acids (PAA) comprising at least hydrophilic repeating neutral amino acids (AANI), other titan aspangine, and hydrophobic repeating neutral amino acid (ANNO); wherein the AANI are identical to or different from one another and the AANO are identical to or different from one another;
   are stable in the aqueous phase at a pH of between 4 and 13 in the absence of a surfactant;
   have a degree of polymerization (DP) between 50 and 200;
   spontaneously associate with at least one active principle when at least one active principle in the undissolved state is added to the colloidal suspension; and
   when associated with at least one active principle, release it in a prolonged manner, in a delayed manner; or in a prolonged and delayed manner.

2. The colloidal suspension of claim 1, wherein the constituent PAA of the particles are block PAA comprising block AANO and block AANI in which;
   the molar ratio of ANNO/(ANNI+AANO) is ≧6%, and
   the absolute length of the AANO block is ≧5.

3. The colloidal suspension of claim 1, wherein the degree of polymerization (DP) is between 60 and 150.

4. The colloidal suspension of claim 3, wherein the constituent PAA of the particles are random copolymer PAA in which:
   the molar ratio of AANI/(ANNI+AANO) is ≧10% and and the molecular weight is ≧2000 Da.

5. The colloidal suspension of claim 3, wherein the hydrophilic repeating neutral amino acids are natural amino adds, rare or synthetic neutral amino acids, or derivatives of neutral amino acids.

6. The colloidal suspension of claim 3, wherein the hydrophobic repeating neutral amino acids are natural neutral amino acids, rare or synthetic neutral amino acids, or derivatives of polar amino acids.

7. The colloidal suspension of claim 3, wherein the particles have a mean size between 0.01 and 0.5 μm.

8. The colloidal suspension of claim 3, wherein the colloidal suspension is aqueous.

9. A pulverulent solid comprising submicron particles, wherein the pulverulent solid is obtained by removing liquid from the colloidal suspension of claim 3.

10. The colloidal suspension of claim 1, wherein the AANI is selected from the group consisting of serine, threonine, hydroxyproline, glutamine, methionine S-oxide, O-glycosidylserine, N-hydroxyethylasparagine, N-hydroxypropylglutamine, N-hydroxyethylglutamine, and N-hydroxypropylasparagine.

11. The colloidal suspension of claim 10, wherein the AANI is glutamine.

12. The colloidal suspension of claim 1, wherein the AANO is selected from the group consisting of leucine, isoleucine, valine, alanine, proline, phenylalanine, norleucine, norvaline, methyl glutamate, ethyl glutamate, benzyle aspartate and N-acetyllysine.

13. A method of preparing a stable colloidal suspension of submicron particles associated with at least one active principle, comprising contacting at least one active principle in the solid state with the colloidal suspension of particles of claim 1, to thereby obtain a stable colloidal suspension of submicron particles associated with at least one active principle.

14. A method of preparing a stable colloidal suspension of submicron particles associated with at least one active principle, comprising contacting the colloidal suspension of particles of claim 1 with a liquid phase containing at least one active principle, to thereby obtain a stable colloidal suspension of submicron particles associated with at least one active principle.

15. A stable colloidal suspension comprising submicron particles, wherein the particles:
   are individualized supramolecular arrangements comprising linear, peptide-linked, amphiphilic polyamino acids (PAA) comprising at least hydrophilic repeating neutral ammo acids (AANI), other than asparagine, and hydrophobic repeating neutral amino acid (ANNO); wherein the AANI are identical to or different from one another and the AANO are identical to or different from one another;
   are stable in the aqueous phase at a pH of between 4 and 13 in the absence of a surfactant;
   have a degree of polymerization (DP) between 50 and 200;
   are spontaneously associated with at least one active principle; and
   release said active principle in a prolonged manner, in a delayed manner, or in a prolonged and delayed manner.

16. A pulverulent solid comprising submicron particles, wherein the pulverulent solid is obtained by removing liquid from the colloidal suspension of claim 15.

17. The colloidal suspension of claim 15, wherein the at least one active principle is a vaccine, a protein, a peptide, a polysaccharide, a nucleic acid, an anticancer chemotherapeutic, or a mixture thereof.

18. The colloidal suspension of claim 15, wherein the at least one active principle is a hemoglobin, a cytochrome, an albumin, an interferon, an antigen, an antibody, erythropoietin, insulin, a growth hormone, factor VIII, factor IX, an interleukin, a hematopoiesis-stimulating factor, heparin, an RNA, a DNA, an anthracycline, a taxoid, or a mixture thereof.

19. The colloidal suspension of claim 15, wherein the at least one active principle further comprises a pharmaceutical, nutritional, plant-protective, or cosmetic active principle.

20. A method of preparing a stable colloidal suspension of submicron particles, comprising contacting a pulverulent solid comprising submicron particles, wherein the particles:
- are individualized supramolecular arrangements comprising linear, peptide-linked, amphiphilic polyamnino acids (PAA) comprising at least hydrophilic repeating neutral amino acids (AANI), other than asparagine, and hydrophobic repeating neutral amino acid (ANNO); wherein the AANI are identical to or different from one another and the AANO are identical to or different from one another;
- are stable in the aqueous phase at a pH of between 4 and 13 in the absence of a surfactant;
- have a degree of polymerization (DP) between 50 and 200;
- spontaneously associate with at least one active principle when at least one active principle in the undissolved state is added; and
- when associated with at least one active principle, release it in a prolonged manner, in a delayed manner, or in a prolonged and delayed manner, with an aqueous medium, to thereby obtain a stable colloidal suspension of submicron particles.

21. A method of preparing a stable colloidal suspension of submicron particles associated with at least one active principle, comprising contacting a pulverulent solid comprising submicron particles, wherein the particles:
- are individualized supramolecular arrangements comprising linear, peptide-linked, amphiphilic polyamino acids (PAA) comprising at least hydrophilic repeating neutral amino acids (AANI), other than asparagine, and hydrophobic repeating neutral amino acid (ANNO); wherein the AANI are identical to or different from one another and the AANO are identical to or different from one another;
- are stable in the aqueous phase at a pH of between 4 and 13 in the absence of a surfactant;
- have a degree of polymerization (DP) between 50 and 200 with a liquid phase containing at least one active principle, to thereby obtain a stable colloidal suspension of submicron particles associated with at least one active principle, and wherein said particles are spontaneously associate with said active principle; and
- release said active principle in a prolonged manner, in a delayed manner, or in a prolonged and delayed manner.

22. A method of preparing a stable colloidal suspension of submicron particles associated with at least one active principle, comprising mixing a pulverulent solid comprising submicron particles, wherein the particles:
- are individualized supramolecular arrangements comprising linear, peptide-linked, amphiphilic polyamino acids (PAA) comprising least hydrophilic repeating neutral amino acids (AANI), other than asparagine, and hydrophobic repeating neutral amino acid (ANNO); wherein the ANNI are identical to or different from one another and the AANO are identical to or different from one another;
- are stable in the aqueous phase at a pH of between 4 and 13 in the absence of a surfactant;
- have a degree of polymerization (DP) between 50 and 200 with at least one active principle in the solid stare and then dispersing this mixture of solids in a liquid phase, to thereby obtain a stable colloidal suspension of submicron particles associated with at least one active principle and wherein said particles are spontaneously associated with said active principle; and
- release said active principle in a prolonged manner, in a delayed manner, or in a prolonged and delayed manner.

23. A method of preparing a pulverulent solid comprising submicron particles, comprising:
a) forming a copolymer by copolymerizing monomers formed of amino acid N-carboxy anhydrides (NCA) of at least types (i) and (ii), wherein;
  type (i) NCA monomers comprise NCA-Glu-OR (R-alkyl), NCA-Asp-OR (R=alkyl), NCA forms of hydrophilic neutral amino acids (NCA-AANI) or mixtures thereof, and
  type (ii) NCA monomers comprise NCA forms of hydrophobic neutral amino acids (NCA-ANNO), wherein the copolymerization is carried out in a liquid medium comprising at least one non-aromatic polar solvent selected from the group consisting of N-methylpyrrolidone (NMP), dimethylformamide (DMF), dimethyl sulfoxide (DMSO), dimethylacetamide (DMAc) and pyrrolidone, and optionally at least one cosolvent selected from the group consisting of aprotic solvents, protic solvents, water and alcohols;
b) if any of the NCA monomers of (a) comprise NCA-Glu-OR (R=alkyl), NCA-Asp-OR (R=alkyl), or NCA-Glu-OR and NCA-Asp-OR (R=alkyl), then contacting the copolymer formed in (a) with an aqueous phase comprising at least one amine to convert Glu-OR to Gln and Asp-OR to Asn;
c) optionally dialyzing the liquid medium to purify an aqueous suspension of submicron particles comprising the copolymer;
d) optionally concentrating the suspension obtained in (c); and
e) removing the liquid medium to obtain a pulverulent solid comprising submicron particles comprising the copolymer;
wherein the particles:
- are individualized supramolecular arrangements comprising linear, peptide-linked, amphiphilic polyamino acids (PAA) comprising at least hydrophilic repeating neutral amino acids (AANI), other than asparagine, and hydrophobic repeating neutral amino acids (AANO); wherein the AANI are identical to or different from one another and the AANO are identical to or different from one another,
- are stable in the aqueous phase at a pH of between 4 and 13 in the absence of a surfactant;
- have a degree of polymerization (DP) between 50 and 200;
- spontaneously associate with at least one active principle when at least one active principle in the undissolved state is added to the colloidal suspension; and
- when associated with at least one active principle, releases it in a prolonged manner, in a delayed manner, or in a prolonged and delayed manner.

24. A pulverulent solid comprising submicron particles produced by the method of claim 23.

* * * * *